United States Patent [19]

Laufenberg et al.

[11] Patent Number: 5,441,611
[45] Date of Patent: Aug. 15, 1995

[54] METHOD FOR DETERMINING AND CONTROLLING THE CONCENTRATION OF ACTIVE SUBSTANCES INCLUDED FOR CLEANING AND DISINFECTION IN AQUEOUS CLEANING AND DISINFECTING SOLUTIONS

[75] Inventors: Alfred Laufenberg, Leobendorf, Austria; Mike Varpins, Viersen, Germany; Alfred Werner-Busse, Duesseldorf, Germany; Friedhelm Siepmann, Essen, Germany

[73] Assignee: Henkel Kommanditgesellschaft auf Aktien, Duesseldorf, Germany

[21] Appl. No.: 196,149

[22] PCT Filed: Aug. 13, 1992

[86] PCT No.: PCT/EP92/01846

§ 371 Date: Apr. 22, 1994

§ 102(e) Date: Apr. 22, 1994

[87] PCT Pub. No.: WO93/04361

PCT Pub. Date: Mar. 4, 1993

[30] Foreign Application Priority Data

Aug. 22, 1991 [DE] Germany .................. 41 27 663.9

[51] Int. Cl.$^6$ ............................................. G01N 27/26
[52] U.S. Cl. ............................... 204/153.13; 204/153.1
[58] Field of Search ............... 204/416, 419, 153.13, 204/153.1; 422/82.03

[56] References Cited

U.S. PATENT DOCUMENTS 3,770,608 11/1973 Kelch et al. .................. 204/195 M
4,211,623 7/1980 Ross, Jr. et al. .................. 204/419
4,550,011 10/1985 McCollum .................. 204/153.13

FOREIGN PATENT DOCUMENTS 0188319 7/1986 European Pat. Off. .
2445525 7/1980 France .

Primary Examiner—John Niebling
Assistant Examiner—Bruce F. Bell
Attorney, Agent, or Firm—Ernest G. Szoke; Norvell E. Wisdom, Jr.; Real J. Grandmaison

[57] ABSTRACT

The invention concerns a method of determining the concentration of an iodine-iodide-containing active substance in aqueous solutions intended for use in the cleaning or disinfection of containers such as bottles, drums, kegs, cases and tanks and/or pipe lines in the food-processing industry, as well as for industrial scale cleaning in continuous washing plants, the concentration of the active substances in the solution being measured by determining the iodine/iodide content of the solution. The invention provides a rapid, reliable and accurate method which is not prone to interference and can be used on a continuous basis. In addition, it makes it possible to automate the process by which the active substance is kept at the required concentration. In particular, the method proposed can be employed in an integrated cleaning-in-place system. These advantages are achieved by the invention by virtue of the fact that the iodide ion concentration in the solution is measured potentiometrically using electrodes which behave selectively toward iodide ions, and the concentration of the active substance calculated from the measurement results obtained, the iodine/iodide concentration lying between 0.1 and 1000 ppm, in particular between 1 and 20 ppm.

20 Claims, No Drawings

METHOD FOR DETERMINING AND CONTROLLING THE CONCENTRATION OF ACTIVE SUBSTANCES INCLUDED FOR CLEANING AND DISINFECTION IN AQUEOUS CLEANING AND DISINFECTING SOLUTIONS

FIELD OF THE INVENTION

This invention relates to a method for determining the concentration of an iodine/iodide-containing active substance in aqueous active-substance solutions used in particular for the cleaning or disinfection of containers, such as bottles, casks, kegs, boxes and tanks, and/or pipes in the food-processing industry and for industrial cleaning in continuous washing installations, the concentration of the active substances in the solution being measured by determination of their iodine/iodide content.

STATEMENT OF RELATED ART

Where detergents are used in the institutional sector, it is desirable for ecological and economic reasons to avoid overdispensing. On the other hand, underdispensing results in unsatisfactory cleaning. This problem becomes difficult to solve if the articles to be cleaned pass continuously through a cleaning or disinfecting bath, as is often the case in institutional cleaning, for example in the washing of bottles, casks, kegs and containers, and in the industrial cleaning of sheet-form metals of textiles. This is because the cleaned or disinfected articles remove detergent or disinfectant from the bath, with the result that the cleaning or disinfecting bath is continuously or periodically topped up with fresh water. The gradually decreasing concentration of detergent or disinfectant is measured and restored to the correct level as required.

In cleaning-in-place (CIP) systems where the detergent or disinfecting solution is used several times, diluting effects also occur through mixed phases during the prerinse and final rinse cycles. In addition, it is essential for the storage of used cleaning solutions, which are normally displaced from the pipes with fresh water, to control the time up to which the returning solution is guided into the storage tank and the time beyond which the concentration of detergent or disinfectant in the final rinse water no longer justifies collection and above all the final rinse time after which the installation can be refilled with foods without any danger of contamination with cleaning or disinfecting chemicals. In cleaning in place, this process is known as phase separation.

In these modes of operation, primary importance is attributed to precise measurement of the concentration of detergent and disinfectant in the cleaning or disinfecting solution or in the final rinse water. During the cleaning process, the concentrations of active substances have to be kept within narrow limits for the reasons mentioned above. For example, excessive concentrations in the cleaning of refillable PET bottles (PET=polyethylene terephthalate) lead to stress cracking. If the concentrations are too low, the bottles are again attacked and the cleaning result is unsatisfactory. In cleaning in place, the last step is often a disinfecting step. The contamination of foods with the often toxic disinfectants has particularly to be avoided so that the final rinse has to be monitored with particular care.

Unfortunately, known methods for determining concentrations have disadvantages. Conductivity measurement is carried out as an on-line measuring method. To ensure that variations in conductance in the tapwater do not lead to measurement errors, the safe application of this method presupposes a relatively high conductance of the active-substance solution of typically 3 to 4 mS (milli-Siemens) which is achieved solely by highly alkaline or highly acidic solutions. The absence of suitable on-line methods for measuring substantially neutral active-substance solutions, for example disinfectants based on quaternary ammonium compounds or biguanides (chlorhexidine gluconate) makes them very difficult to use for cleaning in place in the food industry. If conductivity is used as a measure of the active-substance concentration in bottle washing machines, the results obtained mistakenly reflect an excessive active-substance concentration because the conductivity of the solution gradually increases through the introduction of carbon dioxide and through salts obtained, for example, from the dissolution of aluminum foil.

Another method typically used in practice for dispensing active-substance concentrates is proportional dispensing relative to the throughput of bottles. This method is based on the premise that each bottle with the bottle cell removes a constant quantity of wash liquor from the bath. However, this quantity varies according to the degree of scaling of the bottle cells, the foaming behavior of the solution and the guiding of the liquid streams between the various baths of industrial bottle washing machines. It is known from practical experience that, where dosing is carried out by the methods mentioned, the actual concentration of detergent can differ by 50% or more from the required concentration after only a few days. If there are any technical defects in the dosing system, they can only be detected and eliminated after the complicated process of manual concentration measurement carried out at intervals of 1 to 5 days. In cases such as these, variations in concentration by a factor of up to 40 occur in practice.

Other methods of determination in which the content of active substance is determined by chemical analysis are more accurate than conductivity measurement. However, these processes are time-consuming, can only be carried out manually and are unable to measure the concentration continuously. Thus, the concentration of iodine/iodide-containing active substances in the active-substance solution can be measured by determination of the iodine present in the solution. The wetting agent is removed from a sample of the solution by filtration with active carbon. The iodine ions present in the solution are oxidized. Any protein present is bound by addition of copper sulfate. After extraction of the iodine in chloroform or methylene chloride, the iodine content is photometrically determined. The active-substance concentration can be determined therefrom using a calibration curve. Apart from the disadvantages mentioned above, this method is very time-consuming and has a definite tendency to go wrong. Another disadvantage lies in the necessary use of chlorine-containing solvents.

A particular problem resides in the presence of impurities in the active-substance solution which can falsify the measurements obtained. Accordingly, a number of possible methods for determining concentration cannot be used sufficiently reliably in practice.

DESCRIPTION OF THE INVENTION

Object of the Invention

Accordingly, the problem addressed by the present invention was to provide a method of the type mentioned at the beginning which would operate reliably, accurately, quickly and continuously with little tendency to go wrong. Another object of the invention was to enable replenishment of the active substance to be automated. More particularly, the method according to the invention would be suitable for use in an integrated cleaning technique known as cleaning in place. Cleaning in place is based on the use of large, coherent, fully automatic cleaning systems which automatically clean all storage tanks and pipe systems after each production cycle. The cleaning processes are monitored by minicomputers, so that hygiene is always kept up to a predetermined optimal standard. This technique is used in dairies, breweries and in the beverage industry.

Summary of the Invention

According to the invention, the solution to this problem is characterized in that the concentration of iodine ions in the solution is potentiometrically measured by electrodes which respond selectively to iodine ions and the concentration of active substance is determined from the measurements obtained, the concentration of iodine/iodide in the solution amounting to between 0.1 and 1,000 ppm. More particularly, the iodine/iodide concentration in the solution is between 1 and 20 ppm.

DESCRIPTION OF PREFERRED EMBODIMENT

The method according to the invention is advantageously used for measuring the active-substance concentration in the liquor baths and water zones of industrial bottle washing machines.

The method according to the invention may also be used with advantage for measuring the active-substance concentration of detergent or disinfectant solutions for CIP processes in the food industry.

In another advantageous embodiment, the method according to the invention is used to measure the active-substance concentration in industrial continuous washing installations, more particularly for cleaning sheet-form metals or textiles, the articles to be cleaned removing part of the active-substance solution from the baths as they pass through.

The concentration of active substance is preferably determined from the measured potential by means of a calibration curve which has been established by the measured potentials of at least two different concentrations of the active substance in the solution to be monitored. Particularly reliable measurements are obtained because the solution present in practice containing the typical impurities of the particular cleaning and disinfection process is used for calibration. In one particularly advantageous embodiment, the measuring points used for calibration encompass a concentration range between one and two decades.

Direct potentiometry is particularly advantageous for carrying out the method according to the invention because it immediately gives relevant measurements without much complication. In addition, it can readily be integrated into an automatic dispensing system. For calibration, it is advisable to plot the potentials obtained against the logarithm of the concentrations so that a linear calibration curve is obtained.

Another aspect of the invention relates to the dispensing/redispensing of an iodine/iodide-containing active substance into an aqueous active-substance solution. According to the invention, the dosing process is controlled by a control system which compares the actual concentration determined in accordance with the invention with a required concentration determined in advance. An integrated cleaning technique (cleaning in place) can be built up using this method of dosing.

In another preferred embodiment of the invention, prerinse or final rinse waters in CIP processes are separated from the aqueous active-substance solution (phase separation) by controlling the phase separation process by a system which compares the active-substance concentration determined with a required concentration determined in advance and actuates phase separation valves in accordance with the result of the comparison. Test results obtained with the method according to the invention are described in detail in the following.

In a bottle washing machine for refillable PET bottles, concentration measurements were carried out with electrodes responding selectively to iodide ions. To verify the reliability of the new method, the detergent concentration was also determined photometrically as described above for comparison.

An iodide electrode and a conventional pH electrode as counterelectrode were installed in a flow cup. The wash liquor from an operating bottle washing machine was passed through the cup. The amplified measuring signals were recorded on a recorder. A calibration curve was first recorded in which the potential of the original liquor and the potential of the liquor alter an increase in the detergent concentration by a factor of 10 were measured. The concentration of the detergent in the original liquor was photometrically determined. The linear calibration curve was established by plotting the logarithm of the potentials against the concentration. To determine the correlation of the potentiometrically measured concentration values with the photometrically measured values over a broad range, detergent was added in portions during the measurement. The detergent used was the commercial product P3-Stabilon AL flüissig (liquid), a bottle-washing detergent concentrate which is also suitable for the removal of aluminum foils, labels and caps. The results obtained are set out in Table 1 for a soiled detergent solution and in Table 2 for a fresh detergent solution. They clearly reflect the reliability and accuracy of the method according to the invention and hence its outstanding suitability for practical application.

TABLE 1

| Content of P3-Stabilon in % in soiled solution | |
|---|---|
| Photometric | Potentiometric |
| 0.012 | 0.012 |
| 0.025 | 0.022 |
| 0.075 | 0.074 |
| 0.105 | 0.100 |
| 0.140 | 0.135 |
| 0.150 | 0.149 |

TABLE 2

| Content of P3-Stabilon in % in fresh solution | |
|---|---|
| Photometric | Potentiometric |
| 0.012 | 0.014 |
| 0.060 | 0.073 |
| 0.100 | 0.100 |
| 0.140 | 0.131 |

TABLE 2-continued

| Content of P3-Stabilon in % in fresh solution | |
|---|---|
| Photometric | Potentiometric |
| 0.170 | 0.180 |
| 0.210 | 0.195 |

We claim:

1. A method for determining the concentration of an iodine or iodide-containing active substance in aqueous active-substance solutions which are used for the cleaning and disinfection of containers, bottles, casks, kegs, boxes and tanks, pipes in a food-processing industry and for industrial cleaning in continuous washing installations, comprising measuring the concentration of the active substance in the solutions by determination of their iodine or iodide content, wherein the concentration of iodine ions in the solutions is measured potiometrically by electrodes which respond selectively to iodine ions and the concentration of the active substance is determined from the measurements obtained, the iodine or iodide concentration in the solutions being between 0.1 and 1,000 ppm.

2. A method as claimed in claim 1, wherein the iodine or iodide concentration in the solution is between 1 and 20 ppm.

3. A method as claimed in claim 2, wherein the method for measuring the active-substance concentration is used in the liquor baths and water zones of industrial bottle washing machines.

4. A method as claimed in claim 2, wherein the method for measuring the active-substance concentration of detergent or disinfectant solutions is used for cleaning in place processes in the food industry.

5. A method as claimed in claim 4, wherein the active-substance concentration is determined from the measured potential using a calibration curve which has been established by the measured potentials of at least two different concentrations of the active substance in the solution to be monitored.

6. A method as claimed in claim 3, wherein the active-substance concentration is determined from the measured potential using a calibration curve which has been established by the measured potentials of at least two different concentrations of the active substance in the solution to be monitored.

7. A method as claimed in claim 2, wherein the method for measuring the active-substance concentration is used in industrial continuous washing installations for cleaning of sheet-form metals or textiles where articles to be cleaned remove part of the active-substance solution from washing baths as they pass through.

8. A method as claimed in claim 1, wherein the method for measuring the active-substance concentration is used in industrial continuous washing installations where articles to be cleaned remove part of the active-substance solution from the washing baths as they pass through.

9. A method as claimed in claim 8, wherein the active-substance concentration is determined from the measured potential using a calibration curve which has been established by the measured potentials of at least two different concentrations of the active substance in the solution to be monitored.

10. A method as claimed in claim 9, wherein the concentrations used for calibration encompass a concentration range between one and two decades.

11. A method as claimed in claim 10, wherein regular potentiometry is applied.

12. A method as claimed in claim 11, wherein the iodine or iodide-containing active substance is dispensed into an aqueous active-substance solution, and dispensing thereof is controlled by a control system which compares the actual concentration determined with a required concentration determined in advance.

13. A method as claimed in claim 11, wherein prerinse and final rinse waters in cleaning-in-place processes are separated from the aqueous active-substance solution by controlling phase separation by a system which compares the determined concentration of the active substance with a required concentration determined in advance and actuates phase separation valves in accordance with the result of the comparison.

14. A method as claimed in claim 1, wherein the method for measuring the active-substance concentration is used in the liquor baths and water zones of industrial bottle washing machines.

15. A method as claimed in claim 1, wherein the method for measuring the active-substance concentration of detergent or disinfectant solutions is used for cleaning in place processes in the food industry.

16. A method as claimed in claim 1, wherein the active-substance concentration is determined from the measured potential using a calibration curve which has been established by the measured potentials of at least two different concentrations of the active substance in the solution to be monitored.

17. A method as claimed in claim 16, wherein the concentrations used for calibration encompass a concentration range between one and two decades.

18. A method as claimed in claim 1, wherein regular potentiometry is applied.

19. A method as claimed in claim 1, wherein the iodine or iodide-containing active substance is dispensed into an aqueous active-substance solution, and dispensing thereof is controlled by a control system which compares the actual concentration determined with required concentration determined in advance.

20. A method as claimed in claim 1, wherein prerinse and final rinse waters in cleaning-in-place processes are separated from the aqueous active-substance solutions by controlling phase separation by a system which compares the determined concentration of the active substance with a required concentration determined in advance and actuates phase separation valves in accordance with a result of the comparison.

* * * * *